US008304751B2

(12) United States Patent
Honda et al.

(10) Patent No.: US 8,304,751 B2
(45) Date of Patent: Nov. 6, 2012

(54) CHARGED PARTICLE BEAM IRRADIATION APPARATUS

(75) Inventors: Taizo Honda, Tokyo (JP); Hisashi Harada, Tokyo (JP); Yuehu Pu, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 261 days.

(21) Appl. No.: 12/812,486

(22) PCT Filed: May 12, 2008

(86) PCT No.: PCT/JP2008/058725

§ 371 (c)(1), (2), (4) Date: Jul. 12, 2010

(87) PCT Pub. No.: WO2009/139037

PCT Pub. Date: Nov. 19, 2009

(65) Prior Publication Data

US 2010/0288946 A1 Nov. 18, 2010

(51) Int. Cl.
*G21K 5/04* (2006.01)

(52) U.S. Cl. ........... 250/492.3; 250/492.1; 600/1; 600/2

(58) Field of Classification Search ............... 250/492.1, 250/492.2, 492.3; 600/1, 2
See application file for complete search history.

(56) References Cited

U.S. PATENT DOCUMENTS

| | | | | |
|---|---|---|---|---|
| 6,087,672 | A * | 7/2000 | Matsuda et al. | 250/505.1 |
| 2003/0160189 | A1 | 8/2003 | Matsuda | |
| 2010/0006778 | A1 * | 1/2010 | Flynn et al. | 250/492.3 |

FOREIGN PATENT DOCUMENTS

| | | | |
|---|---|---|---|
| JP | 10-314324 | A | 12/1998 |
| JP | 2000-084097 | A | 3/2000 |
| JP | 2003-255093 | A | 9/2003 |

OTHER PUBLICATIONS

Akagi et al. "Ridge Filter Design for Proton Therapy at Hyogo Ion Beam Medical Center", Physics in Medicine and Biology 48 (2003) pp. 301-312.*

International Search Report for PCT/JP2008/058725, completed May 27, 2008.

* cited by examiner

*Primary Examiner* — David A Vanore
*Assistant Examiner* — Nicole Ippolito
(74) *Attorney, Agent, or Firm* — Buchanan Ingersoll & Rooney PC

(57) ABSTRACT

In a charged particle beam irradiation apparatus to be adapted to a particle beam cancer treatment system or the like, a desired depth dose distribution is highly precisely created. In the charged particle beam irradiation apparatus that irradiates a particle beam, which is radiated from a particle beam generation unit, to a subject to be irradiated via a ridge filter exhibiting a cyclic thickness distribution for causing the particle beam to exhibit a desired energy distribution, the ridge filter has plural ridges thereof arranged to be perpendicular to entering directions of the particle beam.

6 Claims, 3 Drawing Sheets

CHARGED PARTICLE BEAM IRRADIATION APPARATUS

TECHNICAL FIELD

The present invention relates to a charged particle beam irradiation apparatus employing a ridge filter and being included in a particle beam cancer treatment system or the like.

BACKGROUND ART

A conventional charged particle beam irradiation apparatus described in patent document 1 uses a ridge filter, which has ridge portions and valley portions, to create a desired distribution in particle-beam energy so that a point at a depth in a subject to be irradiated which a particle beam reaches can have a desired width, and thus creates a dose distribution in a depth direction.

Patent document 1: JP-A-10-314324

DISCLOSURE OF THE INVENTION

Problems to be Solved by the Invention

The charged particle beam irradiation apparatus included in a particle beam cancer treatment system or the like includes a beam radiation-field expansion unit that forms a desired radiation field in a direction orthogonal to a beam axis of a particle beam, and a ridge filter that exhibits a cyclic depth distribution for causing the particle beam to exhibit a desired energy distribution. The kinetic energy of the particle beam having passed through the ridge filter varies depending on a position in the ridge filter which the particle beam has passed. Therefore, once the depth distribution of the ridge filter and the size of an area exhibiting the depth distribution are set to desired ones, the energy of the particle beam having passed through the ridge filter exhibits the desired distribution as a whole.

When the particle beam passes through the ridge filter, the particle beam has the advancing direction thereof changed by the beam radiation-field expansion unit. A majority of particles passes in a direction oblique to the beam axis. When the particle beam passes through the ridge filter, a difference from a designed value is produced in a mean value of thicknesses through which the particle beam passes. Accordingly, an energy loss in the particle beam occurring in the ridge filter varies. An obtained energy distribution has a difference from the distribution envisaged in a design.

An object of the present invention is to highly precisely create a desired depth dose distribution in a charged particle beam irradiation apparatus employed in a particle beam cancer treatment system or the like.

Means for Solving the Problems

According to the present invention, in a charged particle beam irradiation apparatus that expands a radiation field of a particle beam radiated from a particle beam generation unit, and irradiates the particle beam to a subject to be irradiated via a ridge filter exhibiting a cyclic depth distribution for causing the particle beam to exhibit a desired energy distribution, the ridge filter has plural ridges thereof arranged to be perpendicular to an entering direction of the particle beam whose radiation field has been expanded.

Advantage of the Invention

In a charged particle beam irradiation apparatus in accordance with the present invention, a ridge filter has plural ridges arranged to be perpendicular to an entering direction of a particle beam whose radiation field has been expanded. Therefore, the precision in an energy distribution in the particle beam having passed through the ridge filter can be upgraded, and a desired depth dose distribution can be highly precisely created.

DESCRIPTION OF REFERENCE NUMERALS

1: particle beam, 2: X-direction transmission source point, 3: second expansion means, 4: first expansion means, 5: ridge filter, 6: ridge filter attachment base, 7: Y-direction transmission source point, 8: wheel, 9: through hole, 10: beam path.

BEST MODE FOR CARRYING OUT THE INVENTION

Embodiment 1

Figure 1:
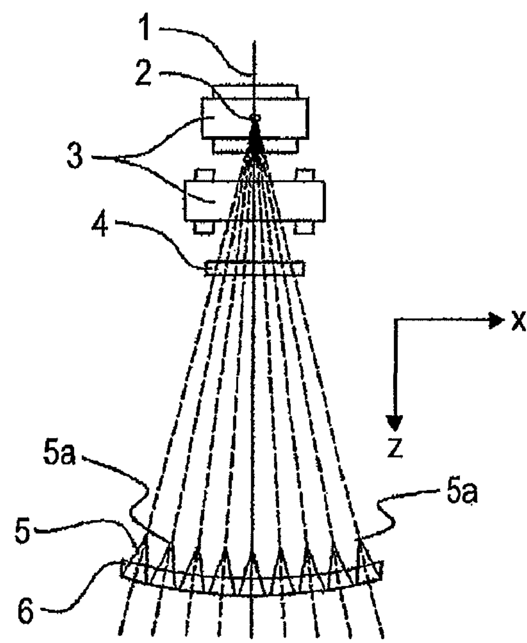
FIG. 1 is a schematic configuration diagram (X-Z section) of a charged particle beam irradiation apparatus in accordance with the first embodiment of the present invention.

FIG. 1 is a schematic configuration diagram (X-Z section) of a charged particle beam irradiation apparatus in accordance with an embodiment 1 of the present invention.

In FIG. 1, a particle beam 1 radiated from a particle beam generation unit (not shown) is irradiated to a subject to be irradiated (not shown) through an X-direction transmission source point 2. The particle beam 1 is expanded by a first expansion means 4, and further expanded by a second expansion means 3.

The expanded particle beam 1 passes through a ridge filter 5 including plural ridges 5*a* such as bar ridges and being attached to a ridge filter attachment base 6.

The particle beam 1 having passed through the ridge filter 5 is reshaped in a desired form by a collimator (not shown), and then irradiated to the subject to be irradiated (not shown).

As shown in FIG. 1, the ridge filter 5 is, as described later, tilted in a particle-beam entering direction at a disposed position on a circle concentric to a circle having the X-direction transmission source point 2 as a center.

Now, the X direction refers to a direction perpendicular to a long-side direction of the ridges 5*a* included in the ridge filter 5.

Next, an operation of the charged particle beam irradiation apparatus in accordance with the embodiment 1 will be described below. First, a particle beam (for example, a proton beam) is generated by the particle beam generation unit (for example, an ion source that generates hydrogen ions). After the proton beam is accelerated by a particle beam acceleration means (not shown), which is realized by a charged particle accelerator or the like, until the proton beam exerts kinetic energy equivalent to an underwater range ranging from about 20 cm to about 30 cm, the proton beam is routed to a particle beam irradiation means by a particle beam transport means (not shown) including a beam optical system composed of an electromagnet and others.

The particle beam 1 routed to the particle beam irradiation means is a proton beam whose kinetic energy is, for example, approximately several hundreds of mega electron volts as mentioned above. The sectional size of the particle beam 1 routed to the particle beam irradiation means normally falls below 1 cm. In order to irradiate such a particle beam to a tumor or the like, the tumor has to be scanned by shifting the position of the particle beam. Otherwise, the beam size has to be expanded.

The particle beam 1 is routed to the first expansion means 4 realized with a scattering body made of lead or tungsten, and scattered by electrons and atoms contained in the scattering body. After passing through the first expansion means 4, the particle beam 1 has the advancing direction thereof dispersed though the particle beam 1 has been concentrated nearly on a forward direction. The particle beam 1 comes to exhibit a predetermined angle distribution. Therefore, the sectional size of the particle beam 1 is expanded to be several centimeters or more when seen at the position of the subject to be irradiated (not shown).

A sufficiently large beam size may not be obtained using only the first expansion means 4 realized with the scattering body. Therefore, the second expansion means 3 realized with a deflection electromagnet is used to further expand the particle beam. The second expansion means 3 may be realized with two deflection electromagnets whose magnetic-field directions are orthogonal to each other. The two deflection electromagnets are excited by alternating-current power supplies for sin ωt and cos ωt and exciting current patterns to be synchronized with each other. Therefore, the particle beam 1 having passed through the second expansion means 3 is deflected as if to draw a circle. The expansion means is an existing conventional technique and referred to as a wobbling electromagnet. The radius of the circle is referred to as a wobbling radius.

Once the ratio of a scattering radius of a particle-beam section provided by the first expansion means 4 to the wobbling radius provided by the second expansion means 3 is adjusted to be equal to a predetermined ratio, a particle-beam distribution that is substantially flat in a transverse direction can be created near the center of a radiation domain. A domain in which the particle-beam distribution is not uniform and which is separated by a predetermined distance from the center of the radiation domain is removed by the collimator (not shown). The collimator is realized with plural foliated plates that has a thickness not permitting the particle beam 1 to pass through and that is made of iron or the like. The arrangement of the foliated plates is controlled so that an opening of the collimator takes on an arbitrary two-dimensional shape. If the two-dimensional shape is matched with the shape of a tumor, a radiation field is created in line with the existing range of the tumor.

By the way, a depth (range) in a human body to which a particle beam propagates is generally determined with the energy of the particle beam. The particle beam rapidly releases its energy near the terminal of the range and comes to a halt. This phenomenon is called a Bragg peak. The phenomenon is utilized in order to kill a tumorous cell existent at a considerable depth from the body surface. The tumor has a thickness in a depth direction. Therefore, for uniformly irradiating a particle beam to the tumor (lesion), it is necessary to perform manipulations for uniformly spreading the Bragg peak in the depth direction of the tumor. The uniformly spread dose is referred to as a spread-out Bragg peak (SOBP).

In order to create a distribution in the depth direction of a radiation field as mentioned above, an energy distribution in the particle beam 1 has to be adjusted. A method that has been adopted in the past and is also employed in the present invention is to pass the particle beam 1 through the ridge filter 5 exhibiting a predetermined depth distribution. The ridge filter 5 can spread the energy distribution in the particle beam within a predetermined range according to the predetermined depth distribution.

Specifically, the energy of the particle beam having passed through the ridge filter varies depending on an incident position of the particle beam 1 on the ridge filter 5. For example, the first passing particle beam is a particle beam having passed through the thickest region of one bar ridge out of plural bar ridges of the ridge filter 5. The second passing particle beam or third passing particle beam is a particle beam having passed through a region equivalent to a valley between two bar ridges out of the plural bar ridges of the ride filter 5.

The particle-beam energy of the first passing particle beam 1 is lower than that of the second or third passing particle beam, and the depth in a subject to be irradiated which the particle beam reaches is shallower. In contrast, the second or third passing particle beam may reach the deepest position in the subject to be irradiated.

As mentioned above, a radiation field having a predetermined width is formed in the depth direction of the subject to be irradiated. The predetermined width is generally determined with a difference between the thickness of the thickest part of the ridge filter 5 and the thickness of the thinnest part thereof. In other words, the individual ridge filter 5 exhibits an inherent SOBP. Incidentally, a width of the Bragg peak spread by the ridge filter in the depth direction of a tumor (namely, the width of the SOBP) normally ranges from 1 cm to 20 cm.

After a predetermined setting parameter is given to each of the first expansion means 4 and second expansion means 3, when the ridge filters 5 exhibiting predetermined SOBPs are combined, a desired three-dimensional dose area is formed in a subject to be irradiated.

For exposing a tumor, it is necessary to highly precisely create a dome distribution in the three-dimensional dose area. In order to make the dose distribution uniform in the three-dimensional does area, the particle beam passing through the ridge filter 5 should preferably enter the ridge filter in parallel with the ridge filter, and a certain percentage of the particle beam defined in a design should pass through the ridge filter material having a thickness defined in the design so as to lose its energy.

However, the orientation of a particle beam entering the ridge filter is deflected during expansion of a beam radiation field by the first expansion means 4 and second expansion means 3. When the particle beam passes through the ridge filter 5, the components of the particle beam are oriented in the most diverse directions in the center of the radiation field. On the edge of the radiation field, the advancing directions of many components of the particle beam are the most external directions. Therefore, on the edge of the radiation field, particles entering the ridge filter in oblique directions become most influential.

As mentioned above, in a place where many components enter obliquely, that is, on the edge of the radiation field, particles do not advance through the ridge filter as they are designed to do. A distribution of energy losses becomes different from a designed distribution thereof. In efforts to resolve the influence of oblique entry of a particle beam on the edge of the radiation field, in the embodiment 1 of the present invention, the plural ridges 5*a* included in the ridge filter 5 are, as shown in FIG. 1, tilted at arranged positions on a circle concentric to a circle, which has the X-direction transmission source point 2 as a center thereof, so that the ridges can be perpendicular to particle-beam entering directions.

Accordingly, the precision in a distribution of values energy, which charged particles lose in the ridge filter 5, can be upgraded. The precision in an energy distribution of particles having passed through the ridge filter can also be upgraded. Therefore, a desired depth dose distribution can be highly precisely created, and the precision in treatment can be upgraded.

As mentioned above, in the embodiment 1 of the present invention, in the charged particle beam irradiation apparatus that expands the radiation field of the particle beam 1 radiated from the particle beam generation unit, and irradiates the particle beam to a subject to be irradiated via the ridge filter 5 exhibiting a cyclic thickness distribution for causing the particle beam to exhibit a desired energy distribution, the plural ridges 5*a* included in the ridge filter 5 are arranged to be perpendicular to particle-beam entering directions. Therefore, the precision in the distribution of values of energy which charged particles lose can be upgraded. Eventually, the precision in the energy distribution among particles having passed through the ridge filter can also be upgraded. Since a desired depth dose distribution can be created, the precision in treatment can be upgraded.

Further, an expanded Bragg peak exhibiting a large flatness domain can be attained over a wide radiation field. In addition, since the distance from the radiation field expansion means to the subject to be irradiated can be shortened, even a compact apparatus can form the wide radiation field.

Embodiment 2

Figure 2:
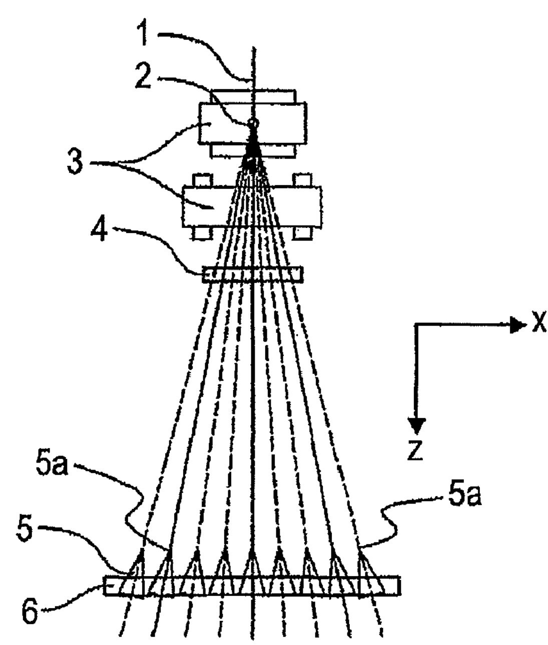
FIG. 2 is a schematic configuration diagram (X-Z section) of a charged particle beam irradiation apparatus in accordance with the second embodiment of the present invention.

FIG. 2 is a schematic configuration diagram (X-Z section) of a charged particle beam irradiation apparatus in accordance with the embodiment 2 of the present invention.

In FIG. 2, the plural ridges 5*a* included in the ridge filter 5 are arranged to be most exactly perpendicular to mean incident particle beam directions on a plane of arrangement (X-Y plane in FIG. 2). In order to compensate an adverse effect on the cyclic thickness distribution of a ridge filter material through which the particle beam passes, the arrangement spacing between ridges may be modulated in a direction in which the ridge filter 5 exhibits the cyclic thickness distribution.

According to the embodiment 2, the precision in creating a depth dose distribution, that is, the precision in treatment can be upgraded. Compared with the embodiment 1, a width (Z direction) necessary to dispose the ridge filter 5 can be decreased.

In the charged particle irradiation apparatus in accordance with the embodiment 1 or 2, a ridge filter including bar ridges is adopted as the ridge filter 5. The present invention is not limited to this type of ridge filter. For example, an existing conical ridge filter may be employed as long as the ridge filter exhibits a cyclic depth distribution permitting obtaining of an SOBP.

Embodiment 3

Figure 3:
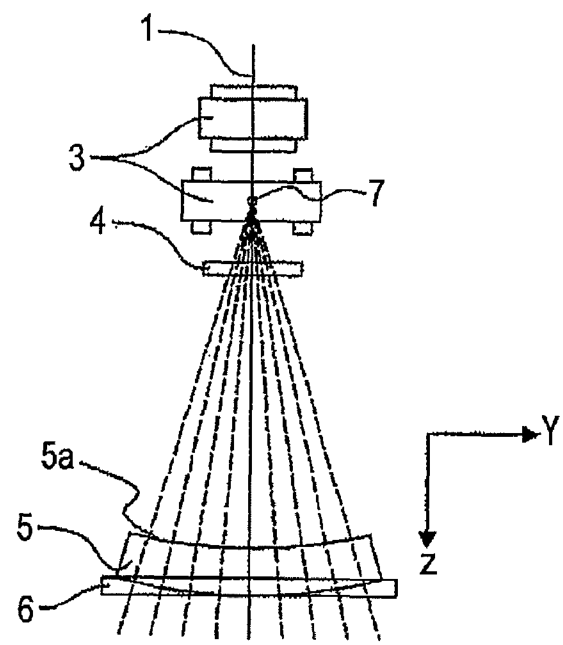
FIG. 3 is a schematic configuration diagram (Y-Z, section) of a charged particle beam irradiation apparatus in accordance with the third embodiment of the present invention.

FIG. 3 is a schematic configuration diagram (Y-Z section) of a charged particle beam irradiation apparatus in accordance with the embodiment 3 of the present invention.

In FIG. 3, as described later, the ridge filter 5 is deformed in such a manner that the plural ridges 5*a* (bar ridges) included in the ridge filter 5 are perpendicular to particle-beam entering directions.

Figure 4:
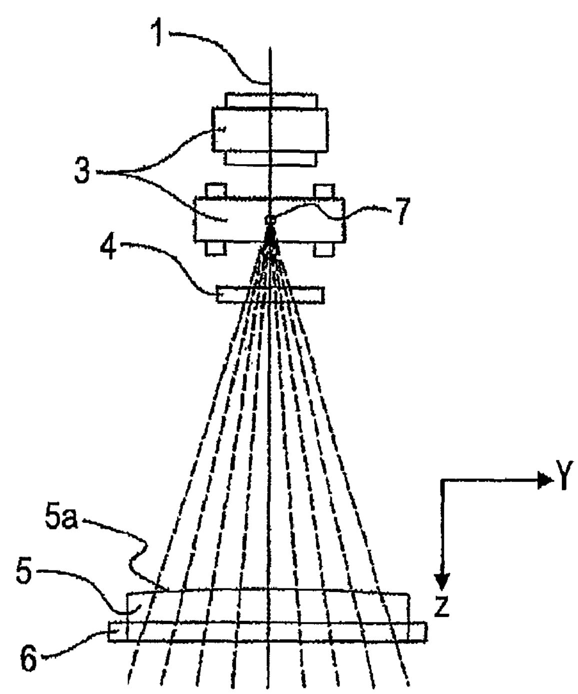
FIG. 4 is a schematic diagram (Y-Z section) of the charged particle beam irradiation apparatus in accordance with the third embodiment of the present invention.

As mentioned previously, in a place where many components of a particle beam enter obliquely, that is, on the edge of a radiation field, particles do not advance through the ridge filter as designed. A distribution of energy losses has a difference from a designed one. In order to resolve an adverse effect of oblique entry of the particle beam on the edge of the radiation field, according to the embodiment 3 of the present invention, as shown in FIG. 3, the ridge shape (Y-axis direction in FIG. 3) of the ridge filter 5 that is normally a linear shape parallel to the Y axis in FIG. 3 is varied depending on a distance from the center of the radiation field in the long-side direction of the ridge filter. The example shown in FIG. 4 has a roof tile shape. A vaulted shape like the one shown in FIG. 4 will do.

According to the embodiment 3, the precision in creating a depth dose distribution, that is, the precision in treatment can be upgraded in a direction (Y-axis direction in FIG. 3) obtained by turning 90° the direction in the embodiment 1.

Embodiment 4

In the aforesaid embodiments 1 to 3, a desired depth expanded radiation domain (SOBP) is obtained under a predetermined radiation-field condition. For cancer treatment, the size of the radiation field and the SOBP have to be varied depending on the size of a tumor. A conventional particle beam treatment system uses different ridge filters for different SOBPs, but uses the same ridge filter under different conditions for radiation-field formation.

In the present embodiment 4, plural ridge filters are prepared for different conditions for radiation-field formation. Any of the ridge filters is selected and disposed on a beam path along which a particle beam passes under a predetermined condition for radiation-field formation.

Figure 5:
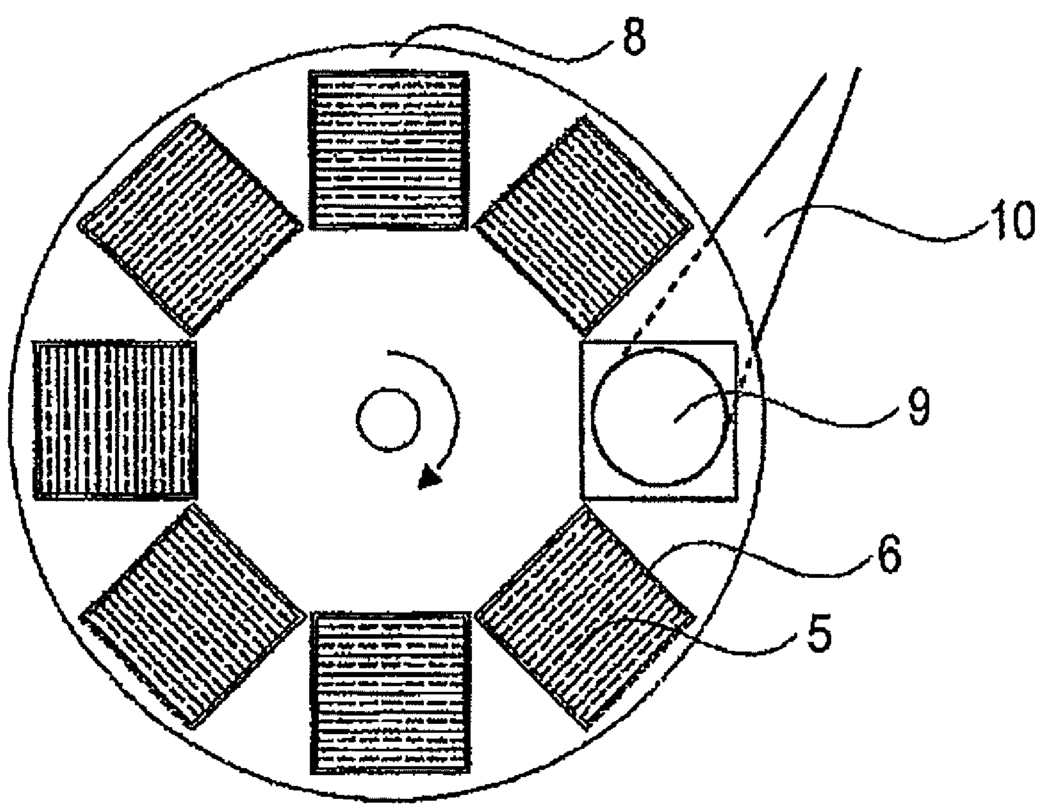
FIG. 5 is a schematic plan view showing a ridge filter replacement unit included in a charge particle beam irradiation apparatus in accordance with the fourth embodiment of the present invention.

FIG. 5 is a schematic plan view showing a ridge filter replacement unit included in a charged particle beam irradiation apparatus in accordance with the embodiment 4. As shown in FIG. 5, plural ridge filters 5 associated with different conditions for radiation-field formation are attached to ridge filter attachment bases 6, and the plural ridge filter attachment bases 6 are mounted on a wheel 8. The wheel 8 is rotated in order to selectively dispose an arbitrary ridge filter attachment base 6 on a beam path 10.

The wheel has a through hole 9 for fear the wheel may hinder inspection such as calibration of a beam axis.

In the present embodiment 4, when a condition for radiation-field formation is a different one, an optimal ridge filter associated with the condition can be selected. Therefore, irradiation can be achieved with a radiation field and SOBP highly precisely determined. The present invention uses a large number of types of ridge filters. By applying the present embodiment, the ridge filters can be readily managed and selected.

In the charged particle irradiation apparatus in accordance with any of the aforesaid embodiments, a wobbler type including the first expansion means and second expansion means is adopted as the expanded radiation field formation unit. The present invention is not limited to the type. A double scattering body type capable of forming an expanded radiation field or a two-dimensional scanning type will do. In addition, the disposed positions of the first expansion means 4 and second expansion means 3 may be switched.

The invention claimed is:

1. A charged particle beam irradiation apparatus that irradiates a particle beam to a subject, comprising:

a particle beam generation unit from which the particle beam is radiated;

a ridge filter, including a plurality of ridges, exhibiting a cyclic thickness distribution for causing the particle beam to exhibit a desired energy distribution, wherein a bottom of each ridge from the plurality of ridges is arranged at an angle different from respective angles of bottoms of the remaining ridges from the plurality of ridges.

2. The charged particle beam irradiation apparatus according to claim 1, wherein a bottom of each ridge from the plurality of ridges of the ridge filter is arranged to be perpendicular to an entering direction of the particle beam.

3. The charged particle beam irradiation apparatus according to claim 1, wherein a bottom of each ridge from the plurality of ridges of the ridge filter is further arranged at a position different from respective positions of bottoms of the remaining ridges from the plurality of ridges.

4. The charged particle beam irradiation apparatus according to claim 1, wherein the ridge filter has the arrangement spacing for each ridge modulated in a direction, in which a cyclic depth distribution is created, according to a change in the angle of each ridge.

5. The charged particle beam irradiation apparatus according to claim 1, wherein each ridge from the plurality of ridges is a bar ridge, and a shape of a bar ridge is varied depending on a distance from the center of a radiation field in the long-side direction of the ridge filter.

6. The charged particle beam irradiation apparatus according to claim 1, wherein a plurality of ridge filters are prepared in association with different conditions for radiation-field formation, and selectively disposed on a beam path, along which the particle beam passes, according to a desired condition for radiation-field formation.

* * * * *